United States Patent [19]
Kemp et al.

[11] Patent Number: 5,591,572
[45] Date of Patent: Jan. 7, 1997

[54] DETECTION OF MAMMALIAN IMMUNODEFICIENCY VIRUSES

[75] Inventors: Bruce E. Kemp, Kew; Carmel J. Hillyard, Paddington; Dennis B. Rylatt, Woodridge; Peter G. Bundesen, Fig Tree Pocket, all of Australia

[73] Assignees: St. Vincents Institute of Medical Research Limited, Victoria; Agen Limited, Queensland, both of Australia

[21] Appl. No.: 157,141

[22] PCT Filed: Jun. 12, 1992

[86] PCT No.: PCT/AU92/00280

§ 371 Date: Feb. 24, 1994

§ 102(e) Date: Feb. 24, 1994

[87] PCT Pub. No.: WO92/22573

PCT Pub. Date: Dec. 23, 1992

[30] Foreign Application Priority Data

Jun. 14, 1991 [AU] Australia .................................. PK6711

[51] Int. Cl.$^6$ .............................. C12Q 1/70; C07K 14/15
[52] U.S. Cl. .............................. 435/5; 435/69.3; 435/975; 530/324; 530/328
[58] Field of Search .................................... 530/324, 326, 530/327, 328, 334; 435/5, 69.3, 975

[56] References Cited

U.S. PATENT DOCUMENTS

| | | | |
|---|---|---|---|
| 4,894,347 | 1/1990 | Hillyard et al. | 436/540 |
| 5,086,002 | 2/1992 | Hillyard et al. | 436/540 |
| 5,177,014 | 1/1993 | O'Connor et al. | 435/188 |

FOREIGN PATENT DOCUMENTS

| | | |
|---|---|---|
| 90/06510 | 6/1990 | WIPO. |
| WO90/13573 | 11/1990 | WIPO. |
| WO92/09632 | 6/1992 | WIPO. |
| WO93/01304 | 1/1993 | WIPO. |

OTHER PUBLICATIONS

Gallaher et al., A General Model for the Transmembrane Proteins of HIV and Other Retroviruses. AIDS Research and Human Retroviruses 5(4):431–440, 1989.

Chong et al., Analysis of Equine Humoral Immune Responses to the Transmembrane Envelope Glycoprotein (gp45) of Equine Infectious Anemia Virus 65(2):1013–1018, 1991.

Gonda et al. Database WPI Section Ch, Week 9013, Derwent Publications Ltd., London, GB; Class B04, AN 90–099193 & US–A–7 408 815, 30 Jan. 1990, Abstract.

Steinman et al. "Biochemical and immunological characterization of the major structural proteins . . . ", *Jnl. of Gen. Virology*, 71(3):701–706, 1990.

Javaherian et al. "Principal neutralizing domain of the human immunodeficiency virus type 1 envelope protein", *Proc. of the Natl. Acad. of Sci.*, 86(17):6768–6772, Sep., 1989.

Talbott et al., "Nucleotide Sequence And Genomic Organization Of Feline Immunodeficiency Virus," *Proc. Natl. Acad. Sci. USA*, vol. 86:5743–5747, (1989).

Olmsted et al., "Nucleotide Sequence Analysis of Feline Immunodeficiency Virus: Genome Organization And Relationship to Other Lentiviruses", *Proc. Natl. Acad. Sci. USA*, vol. 86:8088–8092, (1989).

Garvey et al., "Nucleotide Sequence And Genome Organization of Biologically Active Proviruses of The Bovine Immunodeficiency–like Virus," *Virology*, vol. 175:391–409, (1990).

*Primary Examiner*—Mary E. Mosher
*Assistant Examiner*—Donna C. Wortman
*Attorney, Agent, or Firm*—Foley & Lardner

[57] ABSTRACT

The invention provides peptides having immunological properties in common with the backbone of an immunodominant region of the transmembrane envelope protein of mammalian immunodeficiency viruses, which region comprises a disulphide loop and which region is unexpectedly highly conserved in mammalian immunodeficiency viruses derived from different mammalian sources. The invention also provides method and immunoassay test kits for detection of mammalian immunodeficiency viruses using these above peptides. The invention also relates to antibodies directed against the above peptides, and their use in immunoassays and as immunoadsorbents for mammalian immunodeficiency virus.

16 Claims, 1 Drawing Sheet

DETECTION OF MAMMALIAN IMMUNODEFICIENCY VIRUSES

This invention relates to methods of detection of mammalian immunodeficiency viruses, and in particular to peptides suitable for use in immunoassays for the detection of antibodies to such viruses.

BACKGROUND AND RELATED ART

Since the recognition of human acquired immunedeficiency syndrome (AIDS) in 1981, there has been intensive research into the causal virus, human immunodeficiency virus (HIV), formerly known as human T-cell lymphotropic virus type III (HTLV-III) or lymphadenopathy-associated virus (LAV). It is now known that HIV-specific antibodies are present in the sera not only of most patients with AIDS or AIDS-related complex, but also in the sera of asymptomatic individuals exposed to the virus.

More recently, a variant virus, known as HIV-2, has also been found to be capable of causing AIDS. Immunoassay methods, such as ELISA, utilising various polypeptides encoded by the HIV virus have been extensively used in diagnosis and screening. In most cases the polypeptides are either directly prepared from viral material, or are derived from in vitro expression systems using recombinant DNA technology, although such materials are not ideal. Material derived from viral preparations may be contaminated by viable virus, thus posing a hazard to personnel using the material. Recombinant-derived material may be contaminated by non-HIV protein, resulting in possible loss of specificity.

In an attempt to overcome this problem, polypeptides of HIV have been produced using chemical synthetic means; peptide fragments of a variety of HIV-antigens are disclosed in Australian Patent Application No. 597884 (57733/86) by Genetic Systems Corporation, and in U.S. Pat. Nos. 4,735,896 and 4,879,212, both by United Biomedical Inc. In particular, these three specifications disclose a conserved immunodominant region of gp41 glycoprotein, a region of the major envelope protein of HIV-1. An analogous region of the gp36 protein of HIV-2 has also been synthesised. These regions, which correspond to the transmembrane portion of the envelope protein, enable preferential diagnosis of HIV-1 and HIV-2, and provide assays of very high sensitivity and specificity.

Research on retroviral infections, and in particular those associated with immunodeficiency diseases, has shown that immunodeficiency viruses are widespread among mammalian species. For example, Simian immunodeficiency viruses (SIV strains) have been found in a variety of Old World monkey and ape species, such as macaques, gibbons, and chimpanzees. Similar viruses have been found to infect bovids (bovine immunodeficiency virus, BIV), and felids (feline immunodeficiency virus, FIV). FIV is a retrovirus originally isolated from domestic cats, and has been shown to belong to the same group as HIV (Pederson, N. C. et al; Science (1987) 235 790). This virus has been found in domestic cats in all countries tested, and is associated with similar conditions to those found in AIDS patients; however, the infections seen are only those which normally occur in domestic cats. Fungal infections, such as cryptococcosis, are particularly common, and respond well to symptomatic treatment. Although FIV does not lead to catastrophic infections such as those seen in humans with HIV, and although the virus appears to have been present in the feline population for at least 20 years before its discovery, infection is very widespread and causes significant distress and suffering. There may be other long term implications.

For example, it has recently been found that FIV antibody is widespread in big cats, such as lions, jaguars, leopards and pumas, both in zoo populations and in free ranging animals (Barr M. C., Calle P. R. et al; J. Zoo and Wildlife Med. (1989) 20 285; Sabine M. and Walker C.; Today's Life Science, 1991 3 34). Although in the Australian study by Sabine and Walker contact between the zoo animals and domestic cats could not be ruled out, the zoo cats in the United States in the study by Barr and Calle et al had no contact either with domestic cats or with other infected exotic cats. In contrast to the manifestations of FIV infection in domestic cats, the big cats did not show any correlation between infection with the virus and clinical disease. In view of the fact that many big cat species are in danger of extinction it is of great importance to determine whether FIV infection has any significant impact on the health or breeding efficiency of wild populations.

Although FIV is antigenically unrelated to HIV, and although the sequences of FIV proteins are dissimilar to those of HIV, experience obtained in the development of HIV assays enabled rapid progress in producing an FIV assay. ELISA test kits for FIV, utilising the p26 antigen are commercially available ("Pet Chek"; Idexx Corporation). As in HIV infection, infection with FIV has been found to be followed by production of antibody, together with persistent presence of virus in the host body. However, it has been found using this test that false negatives are more frequent than in analogous tests for HIV virus in humans.

FIV in domestic cats affects T cells in the same manner as HIV in humans. For this reason, FIV has been proposed as an experimental model for AIDS, for example in the testing of vaccines and therapeutic agents. Rapid, accurate diagnosis of FIV is essential for such purposes.

The nucleotide sequence has been reported for 4 strains of FIV. In these known isolates the one sequence is conserved, but there are variations at either end. Two strains from the United States, designated FIV Petaluma and FIV-PPR are described in the following references: Olmsted, R. A., Barnes, A. K., Yamamoto, J. K., Hirsch, V. M., Purcell, R. H. and Johnson, P. R. (1989) Molecular cloning of feline immunodeficiency virus. Proc. Natl. Acad. Sci. USA 86:2448–2452; Olmsted, R. A., Hirsch, V. M., Purcell, R. H. and Johnson, P. R. (1989) Nucleotide sequence analysis of feline immunodeficiency virus: genome organization and relationship to other lentiviruses. Proc. Natl. Acad. Sci. U.S.A. 86:8088–8092; Talbott, R. L., Sparger, E. E., Lovelace, K. M., Fitch, W. M., Petersen, N. C., Luciw, P. A. and Elder, J. H. (1989). Nucleotide sequence and genomic organization of feline immunodeficiency virus. Proc. Natl. Acad. Sci. U.S.A. 86:5743–5747, and two strains from Japan, designated FIV TM1 and FIV TM2, are described in Maki, N., Miyazawa, T., Fukasawa, T., Fukasawa, M., Hasegawa, A., Hayami, M., Miki, K. and Mikami, T. (1992) Arch. Virol. 123:29–45. Molecular characterization and heterogeneity of feline immunodeficiency virus isolates.

The env proteins of these isolates have the following sequence in the transmembrane region:

| Amino Acid No. | Sequence | Isolate |
| --- | --- | --- |
| (678–708) SEQ ID NO:1 | KVEAMEKFLYTAFAMQELGCNQNQFFCEIPKE | PPR |
| (680–711) SEQ ID NO:2 | KVEAMEKFLYTAFAMQELGCNQNQFFCKIPLE | Petaluma |
| (679–710) SEQ ID NO:3 | KVEAIEKFLYTAFAMQELGCNQNQFFCKIPPS | TM1 |
| (799–810) SEQ ID NO:4 | RVRAIEKFLYTAFAMQELGCNQNQFFCKIPPS | TM2 |

Bovine immunodeficiency virus (BIV) is a close relative of HIV which causes AIDS and, like HIV and FIV, is a member of the lentivirus group (Garvey, K. J. et al; Virology (1990) 175 391–409). It cross-reacts antigenically with HIV and can infect cultured human cells. Lentiviruses are readily transmitted in milk to suckling animals. Very recently BIV has been chemically characterised, thus enabling it to be identified and isolated. Investigations are in progress in the U.S.A. into its association with chronic ill health in cattle herds (Whetstone, C. A. et al; Arch. Virol. 1991 (in press)).

BIV causes a large increase in the proportion of white blood cells, which can be mistaken for a cancer caused by Bovine Leukemia Virus (BLV). BIV was first discovered in 1972, when VanDerMaaten et al (VanDerMaaten et al; Journal of the National Cancer Institute (1972) 49 1649–1657) found a virus in cattle which they named bovine visna virus. The name was changed to bovine immunodeficiency virus after it was found that it would infect human cells in culture (Georgiades, J. A. et al; J. Gen. Virol. (1978) 38 375–381), it cross-reacted antigenically with HIV (Amborski, G. F. et al; Veterinary Microbiology (1989) 20 247–253), and it was phylogenetically closer to HIV than to visna (Gonda, M. A. et al; Nature (London) (1987) 330 388–391).

Because the presence of HIV can exacerbate the effects of fungal, microbial and viral infections, as well as cancers which are normally kept under control by the immune system, it is likely that BIV has a similar influence on chronic diseases and some cancers in cattle. In a paper just published by the U.S. Department of Agriculture it was found that in one herd of "poor doers" 34 out of 78 had antibodies to BIV, and in a survey of 1997 mainly dairy cattle from eight states in the southern U.S.A. a prevalence of 4% BIV was determined (Whetstone, C. A. et al; Journal of Virology (1990) 64 3557–3561).

It is a reasonable assumption that the economic consequences of BIV, as with the lentiviruses in other species, will be indirect and are likely to involve other microorganisms. Based on associations with HIV, obvious conditions which may indicate the presence of BIV are: chronic ill thrift, chronic diarrhoea, herds with a history of cancer, severe Johne's disease, persistent mycoplasmal infections, and Jembrana disease in Bali cattle. Until the prevalence of BIV is determined and its association with disease ascertained, it is impossible to estimate the economic consequences of allowing BIV to spread, or the feasibility and cost of eliminating it. With efficient, tests and artificial rearing it has been relatively simple to eliminate caprine arthritis encephalitis virus and visna from goat and sheep flocks, at relatively low cost.

Another possible economic consequence of BIV is public fear of slow viruses, especially in Europe where bovine spongiform encephalopathy (BSE) (mad cow disease) has devastated the British beef industry. Once the fact that lentiviruses related to the AIDS virus can be transferred in milk is known, it is likely that there will be a strong public demand that herds be declared free from BIV. It will not be sufficient for the industry to simply claim that "BIV is not present and that it couldn't possibly have any harmful effect on humans". In Britain over 20,000 cattle have been slaughtered because the failure to control the spread of BSE.

There is thus an urgent need for a rapid, economical test for the detection of antibodies to BIV in cattle, which is suitable for use in large-scale screening of herds. A test kit of this type would be particularly useful in screening herds with a high incidence of chronic ill-health in order to see whether BIV was the underlying cause, and for screening animals to guard against importation of BIV into a hitherto BIV-free herd, geographical area, or country.

The currently available test systems for both BIV and FIV utilise polylpeptide material derived either from whole virus, or from recombinant-derived protein, or alternatively monoclonal antibodies directed against epitopes of such polypeptides. See for example International Patent Applications No. WO 90/13573 and No. WO 90/06510 (corresponding to U.S. Pat. No. 5,219,725), by Idexx Corporation, the entire disclosures of which are incorporated herein by reference. There is therefore an urgent need for a rapid, convenient, and economical assay which utilises a synthetic peptide antigen, in order to reduce costs and to avoid any risk to personnel. In order to avoid unnecessary manipulation of blood samples, which in itself can pose a risk to personnel handling the material, an assay which can be performed on whole blood samples is particularly advantageous. Such an assay is described in our previous Australian patent applications, No. 22224/88 and No. 24182/88 (corresponding to U.S. Pat. Nos. 4,894,347 and 5,086,002), by Agen Limited, and is marketed under the name SimpliRED.

We have now unexpectedly found that it is possible to identify an immunodominant region in the highly conserved region of the transmembrane portion of the envelope protein of a mammalian immunodeficiency virus. This sequence can be synthesised using normal polypeptide synthetic methods, and can be used in immunoassays to detect antibody directed against the virus. This finding is particularly surprising in view of the known differences in the proteins and in the antigenicity of immunodeficiency viruses from different species.

SUMMARY

According to one aspect of the invention there is provided a disulphide loop peptide of an immunodominant region of an envelope protein of a mammalian immunodeficiency virus.

Preferably the peptide is derived from an immunodeficiency virus infecting either an ungulate or a felid. For the purposes of this specification, "ungulate" is to be taken to include the whole of the family Ungulata, for example bovids, including cattle, buffalo, water buffalo and yaks; sheep; goats; horses; camels; deer, including reindeer, red deer, fallow deer, and roe deer; antelopes; llamas; alpacas; vicunas; and guanacos. The terms "felids" is to be understood to include all members of the order Felidae, including domestic cats, lions., tigers, jaguars, leopards, pumas, ocelots etc.

Where the immunodeficiency virus is FIV, the peptide preferably comprises amino acids 680 to 711 of the env gp940 protein of the FIV Petaluma strain, as follows (SEQ ID NO:2):

KVEAMEKFLYTAFAMQELGCNQNQFFCKIPLE, or a sequence of 8 or more, preferably 10 to 20, more preferably 20 to 25, most preferably 25 to 32 amino acids within said sequence.

Where the immunodeficiency virus is BIV, the peptide preferably comprises amino acids 625 to 660 of the env gp42 protein, as follows (SEQ ID NO:5):

RVSYLEYVEEIRQKQVFFGCKPHGRYCH-FDFGPEEV, or a sequence of 8 or more, preferably 10 to 20, preferably 20 to 25, most preferably 25 to 35 amino acids within said sequence.

For both FIV and BIV, other isolates encompassing the respective regions may also be used.

The aforementioned sequences are given in the one-letter amino acid code, as set out in Table 1:

TABLE 1

| Amino acid | One-letter Abbreviation |
| --- | --- |
| Alanine | A |
| Arginine | R |
| Asparagine | N |
| Aspartic acid | D |
| Cysteine | C |
| Glutamic acid | E |
| Glutamine | Q |
| Glycine | G |
| Histidine | H |
| Isoleucine | I |
| Leucine | L |
| Lysine | K |
| Methionine | M |
| Phenylalanine | F |
| Proline | P |
| Serine | S |
| Threonine | T |
| Tryptophan | W |
| Tyrosine | Y |
| Valine | V |

Although a peptide according to the invention may be synthesised using recombinant DNA technology, utilising the corresponding DNA sequence derived from the sequence of the appropriate virus, such as BIV or FIV, it is preferably chemically synthesised, using conventional methods of solid phase peptide synthesis.

According to a second aspect of the invention, there is provided a polyclonal or monoclonal antibody directed against a disulphide loop peptide of an immunodominant region of an envelope protein of a mammalian immunodeficiency virus. Such antibodies may be prepared by a variety of conventional techniques, which are well known in the art. Antibodies which may be used include polyclonal and monoclonal antibodies or immunologically functional fragments thereof, including F(ab), F(ab)$_2$, Fv, single chain Fv, or V$_H$ fragments. Fragments may be prepared by conventional or recombinant DNA methods.

According to a third aspect of the invention, there is provided an immunoassay for detection of antibody against a mammalian immunodeficiency virus in a biological sample from a mmal exposed to said virus, comprising the step of using a reagent comprising a peptide as described above. Preferably the immunoassay is provided in the form of a test kit.

Such assays include for example ELISA, particle agglutination assays, autologous red cell agglutination assays, other agglutination assays, radioimmunoassays, and fluorescent immunoassays. In a particularly preferred embodiment of the invention, the assay is a direct or indirect whole blood agglutination assay, as described in Australian Patent Applications No. 22224/88 and No. 24182/88, (corresponding to U.S. Pat. Nos. 4,794,347 and 5,086,002), the entire disclosures of which are incorporated herein by reference.

According to a fourth aspect of the invention, there is provided an immunoadsorbent for a mammalian immunodeficiency virus, comprising an antibody directed against a peptide as described above.

Although the invention is specifically described by reference to FIV and BIV, it will be clearly understood that the invention includes within its scope corresponding immunodominant regions of the transmembrane portion of the env protein of other mammalian immunodeficiency viruses.

Moreover, it will be understood that the invention includes peptides of subtypes of FIV, BIV or other mammalian immunodeficiency viruses, analogous to HIV-1 and HIV-2.

Furthermore, although the specific peptides referred to above comprise about 35 amino acids including the specified sequences, it is to be understood that provided the conformation recognised by the appropriate antibody is preserved, peptides of the invention may comprise analogues or conservative substitutions for the amino acids recited in the sequence. It is also to be understood that the sequence may either be extended by the addition of further amino acids to either terminus of the above sequence, in particular extensions derived from the known sequence of the appropriate env protein, or alternatively that the sequence may be modified by deletion of amino acids from either terminus.

DETAILED DESCRIPTION OF THE INVENTION

Figure 1:
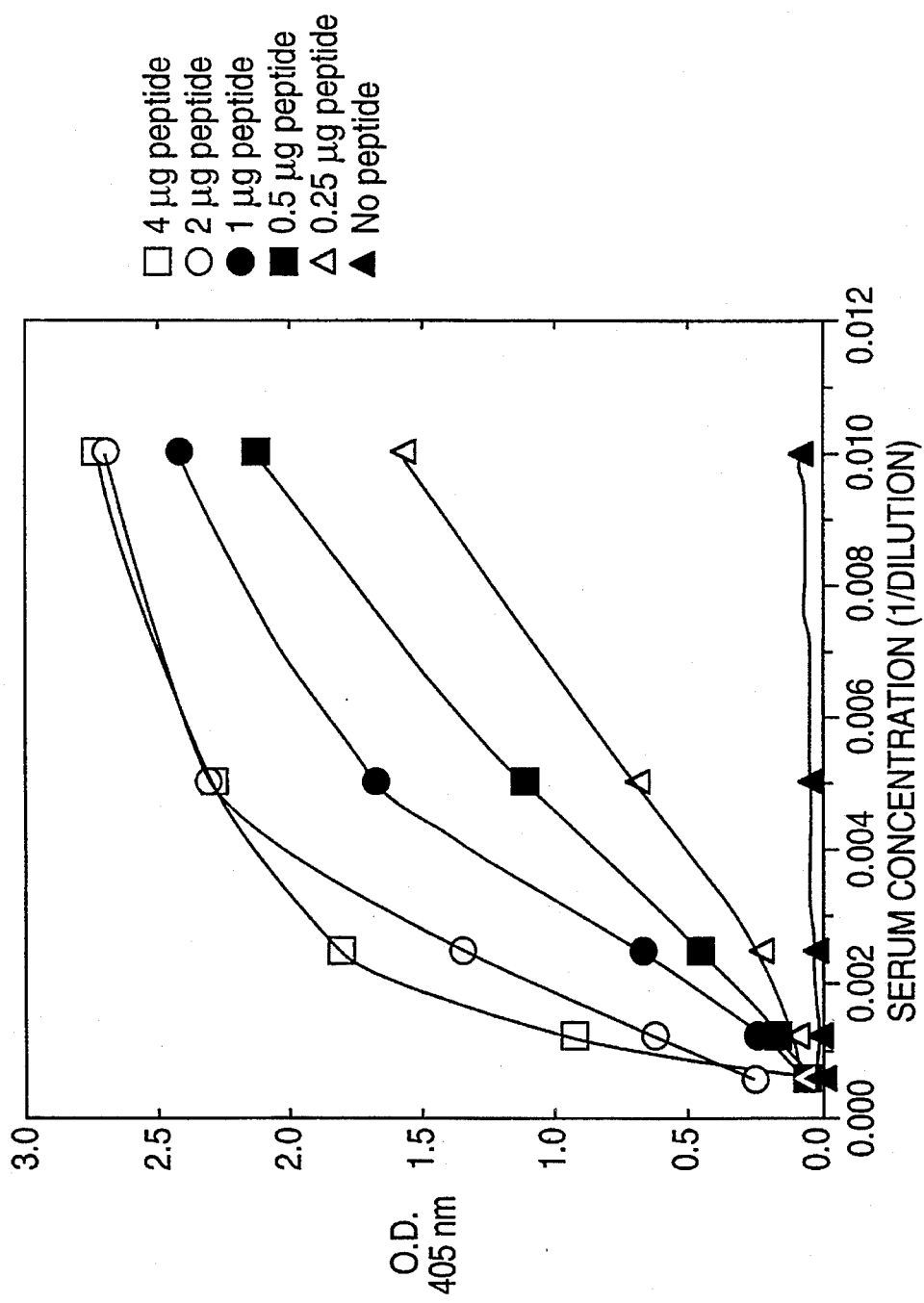
FIG. 1 illustrates the results of an ELISA assay using synthetic FIV peptide antigen and FIV-positive antiserum.

The invention will now be described by way of reference only to the following non-limiting examples, and to the accompanying drawing.

EXAMPLE 1

Synthesis of Peptides

FIV (680–715) and BIV (625–660) as described above were synthesised using the Merrifield method of solid-phase synthesis, using an Applied Biosystems Automated Peptide Synthesiser with Boc-amino acids (Kemp, B. E. et al, Science (1988) 241 1352–1354). Alternative chemistries may be used, for example those using Fmoc or other protected amino acid derivatives, as is well known to those skilled in the art.

Peptides were prepared as their carboxyl terminal amines using 4-methylbenzhydrylamine resin. The peptide was cleaved from the solid-phase resin, and simultaneously deprotected by treatment with anhydrous hydrogen fluoride. The freed peptide was purified by either cation or anion exchange chromatography, depending on its amino acid composition, and then by reverse phase chromatography in either 0.1% trifluoroacetic acid or 0.1M ammonium bicarbonate (Kemp, B. E. and Pearson R. B.; "Design and Use of Peptide Substrates for Protein Kinases" in Protein Phosphorylation (edited by T. Hunter and B. M. Sefton), Methods in Enzymology, 1991 200 121–134.

The peptides synthesised according to this procedure are highly reactive to antibodies to FIV and BIV respectively, add can be used for various immunoassays, including autologous red cell agglutination, particle agglutination, enzyme immunoassay and radioimmnoassay.

Peptides having these sequences contain internal disulphide bonds. They may be used in either the oxidised or the reduced forms, or in conjunction with conjugated or protective groups. For example, they may be conjugated to carrier molecules.

Peptides from BIV p26 antigen are synthesised using the same methods for comparative purposes, and screened for the presence of epitopes, as has previously been performed for FIV (see WO 90/13573).

EXAMPLE 2

ELISA Assay Using Synthetic Peptides of FIV (680–711)

Microtitre plate wells were coated with 0.25 to 1 g peptide in carbonate buffer or in 30% acetic acid. Test sera were incubated in the wells at a dilution of 1:100. The secondary reagent was protein A-horseradish peroxidase. The reaction was developed with ABTS for 20 minutes, and read in a microtitre plate reader at 405 nm. Results were defined as follows:

"Positive" results had optical density greater than 0.3;

"Close" results had optical density between 0.2 and 0.5; and

"Strong" results had optical density between 1.0 and 3.0. Titres from infected cats were commonly between 800 and 1600, but ranged up to 6400.

Results using crude peptide antigen are summarised in FIG. 1. A standard of 1 µg of peptide and a dilution of 1:100 of serum was selected for use in routine screening.

8 kittens were experimentally infected with FIV by subcutaneous injection with a sample of virus isolated in Western Australia, and were tested using the ELISA following inoculation. At two weeks all the kittens were seronegative, but were seropositive after four weeks. Titres peaked after six weeks, and ranged from 400 to 6400.

EXAMPLE 3

Comparison with ELISA Assay for FIV p26 Protein

The ELISA using the 36 amino acid peptide was compared with a commercially-available ELISA based on FIV p26 antigen ("Pet Chek"; Idexx Corporation). This comparison showed a number of discrepant results, as summarised in Table 2.

TABLE 2

|  | 36 amino acid peptide [FIV (680-7/15)] | "Pet CHEK" |
| --- | --- | --- |
| 113 | – | – |
| 44 | + | + |
| 14 | + | – |
| 2 | – | + |

Fourteen of the sixteen discrepant results were close to the cut-off value on one or both tests. The results suggest that the ELISA using the synthetic peptide showed both greater sensitivity, in that it was able to detect positive reactions not shown in the Pet Chek assay, and greater specificity, in that it appears that the latter showed false positives.

EXAMPLE 4

Whole Blood Agglutination Assay

Feline blood samples were also tested using the whole blood agglutination assay as described in Australian Patent Applications No. 22224/88 and 24182/88 (corresponding to U.S. Pat. Nos. 4,894,347 and 5,086,007), and also described in Wilson, K. M. et al, J. Immunol. Methods, 1991 138 119–128, the entire disclosure of which is incorporated by reference herein This method was adapted for use with FIV and cat blood by using the synthetic FIV peptide of the invention, and antibody directed against feline red blood cells. This antibody was prepared by immunisation using conventional methods.

Whole Blood Agglutination Assay Test Kit for FIV

COMPONENTS:

1. Anti-erythrocyte antibody: H74.53.4C1/180 Extinction co-efficient 1.0
2. Anti-peptide antibodies
   a) Affinity column and horseradish peroxidase label: K20.83.4D4/4-91 IgG1. Extinction co-efficient 1.65
   b) Positive control: K21.83.1B5/25 IgM.
3. FIV peptide (SEQ ID NO:2) K V E A M E K F L Y T A F A M Q E L G C N Q N Q F F C K I P L E—NH$_2$, corresponding to an immunodominant region of the major coat protein of FIV 680–711 (gp40)

(a) Preparation of erythrocyte binding molecule H74.53.4C1/180.

The antibody directed against feline red blood cells was prepared using conventional immunisation and screening procedures. Mice were immunised with feline red blood cells, and monoclonal antibodies produced by fusing the spleen cells of immunised animals with mouse myeloma cells. The antibodies were screened by spin agglutination assay. Spin agglutination was performed by a modification of the method of Wyatt & Street, Aust J Med Lab Sci, 4 48–50. 50 µl of cell culture supernatant was mixed with 50 µl of a 1% red blood cell suspension in a microtitre plate. For this example, antibodies which bound glycophorin, but did not agglutinate, were selected. Of 384 wells, 50 primary clones were chosen. Subsequent absorption studies were performed (50 feline whole blood samples) and the monoclonal antibody H74.53.4C1/180 (4C1/180) was selected.

Intact antibody was purified by the Prosep A production method. The purified monoclonal antibody 4C1/180 was digested with 1% w/w pepsin for 40 mins at 37° C. The antibody was acidified with 1/10 12% acetic acid to pH 3.5. The reaction was terminated by the addition of 3.5M Tris buffer pH 8.0 to raise the pH to 8, and the F(ab)$_2$ fragment was purified by S200 gel filtration chromatography.

The F(ab)$_2$ fragments were reduced by incubation with a final concentration of 10 mM mercaptoethylamine for 30 mins at 37° C. The partially reduced Fab fragments were stabilised by reaction with 10 mg/ml DTNB for 30 mins at room temperature followed by addition of a final concentration of 30 mM iodoacetamide for 30 mins at room temperature. The Fab-TNB-Ac fragment produced was then purified on Ultrogel AcA 44 gel filtration chromatography.

(b) FIV Peptide preparation:

The peptide corresponding to an immunodominant region of the major coat protein of FIV 680–711 (gp40) (sequence above) was reduced with 0.5M dithiothreitol for 30 minutes at room temperature. The reaction was terminated by the addition of 10 mM HCl. The mixture was applied to a Sep-pak C18 cartridge (Millipore Waters) that was treated with 10 mls of a 40:60 acetonitrile:HCl solution. The reduced peptide was cycled three times through the Sep-pak, washed with 20 mls of 10 mM HCL before elution with 5 mls of 40:60 acetonitrile:HCl. The reduced peptide was then freeze-dried overnight.

(c) Conjugation of peptide and antibody and purification of the FIV reagent:

The peptide in "b" above was dissolved in 6M guanidine-HCL and mixed with the 4C1/180 Fab-TNB-Ac mixture from (a) above in a 0.5(1.0): 1.0 peptide:antibody molar ratio for 1 min at room temperature. The reaction was terminated by the addition of a final concentration of 30 mM iodoacetamide for 30 mins at room temperature.

Initial purification was performed on an Ultrogel AcA44 gel filtration column to remove free peptide and was followed by affinity purification on an anti-peptide antibody column (K20.83.4D4/4–91) to remove free 4C1/180 antibody. The final purification was then performed on an Ultrogel AcA 44 gel filtration column.

(d) Formulation of FIV reagent and Assay Procedure:

The FIV reagent was formulated to 15 µg/ml in phosphate-buffered saline pH 7.4 containing 10 µg/ml 2-NBA, 0.5% fish gelatin and 0.5 mg/ml 3A1/48 Fab-Ac blocker antibody.

For assay, 10 µl of anticoagulated blood was placed on a plastic slide and 25 µl of FIV reagent added and mixed. The slide was rocked for 2 minutes and the agglutination read. Table 3 and Table 4 show results from testing FIV positive and FIV negative samples respectively.

TABLE 3

Summary of positive samples tested:

| Sample | Number positive | % Sensitivity |
| --- | --- | --- |
| Total Plasma samples | 104/104 | 100% |
| W.A. 2 weeks post infection | 2/12 | 16% |
| W.A. 4 weeks post infection | 12/12 | 100% |
| Chatswood, VPS & SA samples | 7/7 | 100% |
| Total number of samples tested >4 weeks post infection | 104/104 | 100% |

TABLE 4

Summary of FIV negative samples tested:

| Sample | Number negative | % Specificity |
| --- | --- | --- |
| Whole blood | | |
| S.A. Gilles Plains | 47/49* | 95.9% |
| W.A. Preinfection | 24/24 | 100% |
| Chatswood Vet Surgery | 18/18 | 100% |

TABLE 4-continued

Summary of FIV negative samples tested:

| Sample | Number negative | % Specificity |
| --- | --- | --- |
| Plasma | | |
| Negative plasmas | 91/91 | 100% |
| Total samples tested | 180/182 | 98.9% |

*One of these samples was confirmed positive on first collection but negative on subsequent samples.

EXAMPLE 5

Sensitivity and Specificity of ELISA Assay

Using Synthetic Peptides of FIV (620–711)

A further study was performed to assess the sensitivity and specificity of the ELISA assay, using the synthetic peptides of FIV (680–715). Microtitre plate wells were coated with 1 µg peptide in carbonate buffer or in 30% acetic acid. Test sera were incubated in the wells at a dilution of 1:100. The secondary reagent was protein A-horseradish peroxidase. The reaction was developed with 2,2'-azinodi-(3-ethylbenzthiazoline) sulphonic acid (Sigma) for 20 minutes, and read in a microtitre plate reader at 420 nm. Results from testing 91 positive and 91 negative samples are shown in Table 5. Results were defined as follows:

"Negative" results had optical density less than 0.5;

"Close" results had optical density between 0.5 and 1.5; and

"positive" results had optical density greater than 1.5.

TABLE 5

| | Absorbance reading at A 420 nm | | |
| --- | --- | --- | --- |
| Samples | OD 420 nm < 0.5 | OD 420 0.5–1.5 | OD 420 nm > 1.5 |
| Negative plasma Number tested 91 | 87 | 4* | none |
| Positive plasma Number tested 91 | 4** | none | 87 |

*None of these plasmas gave positive agglutination with the FIV reagent (see Example 4)
**One sample was from a 2 week experimental infection, the other 3 samples confirmed negative.

EXAMPLE 7

BIV Peptides

BIV gp42 peptide was tested and compared with BIV p26 antigen as described above for FIV, using both ELISA and whole blood agglutination assays.

BIV protein p25 was chosen as the test antigen for comparison as in experimental infections it was the major antigen detected by Western blotting, and in natural infections antibody to p26 was present in all naturally infected cattle (Whetstone, C. A. et al; Journal of Virology (1990) 64 3557–3561).

Sera from both naturally infected and experimentally infected cattle were tested.

For the whole blood agglutination assay, the peptide identified as most useful in the ELISA assay is conjugated to a monoclonal antibody which binds to bovine erythrocytes.

Advantages of the Invention

The peptide according to the present invention is chemically synthesised or produced by recombinant protein expression without any requirement to use either whole virus or viral lysates. The use of peptides, compared to the use of viral lysates or impure recombinant protein preparations, avoids the problem of false positive results due to contaminating proteins or to non-specific cross-reactivity caused by presence of non-essential regions of viral proteins, which are not necessary for detection. Because the peptides of the preferred embodiment of the present invention are prepared synthetically, the quality can be controlled, thus ensuring reproducibility of the test results. The peptides of this invention have also been found to elicit strong humeral and cellular immune reactions. For example, repeated immunisation of a sheep has elicited immune serum with a titre of 1:50000. They therefore are expected to be useful as immunoabsorbents.

It will be clearly understood that the invention in its general aspects is not limited to the specific details referred to hereinabove.

We claim:

1. A purified peptide of length up to about 35 amino acids that specifically binds to antibodies to feline immunodeficiency virus (FIV) and that corresponds to an immunodominant region of FIV gp40, wherein said peptide includes amino acids 699 to 706 of said gp40, optionally linked to form a disulfide loop.

2. A peptide according to claim 1, which is 36 amino acids in length.

3. A peptide according to claim 1, which has a sequence that corresponds to SEQ ID NO:2.

4. A peptide according to claim 1, which consists of SEQ ID NO:2
KVEAMEKFLYTAFAMQELGCNQNQFFCKIPLE.

5. An immunoassay for detection of antibodies that specifically bind to feline immunodeficiency virus (FIV), in a biological sample from a felid mammal exposed to the virus, comprising the steps of:
  (i) contacting a sample of a biological fluid sample from the mammal with a peptide according to claim 1, said peptide being unbound or bound, labeled or unlabeled, and
  (ii) detecting the formation of immune complex between said peptide and antibodies in said sample.

6. The immunoassay of claim 5, which is a hemagglutination assay; wherein said peptide is coupled to an antibody or antibody fragment which recognizes feline red blood cells; wherein said biological sample is a blood sample; and wherein formation of immune complex is evidenced by agglutination.

7. The immunoassay of claim 6, wherein the coupling between said antibody or antibody fragment and said peptide is between a sulfhydryl group on the antibody or antibody fragment and a sulfhydryl group of at least one of the cysteine residues which are amino acids 699 and 706 of said sequence.

8. The immunoassay of claim 5, wherein said peptide is 36 amino acids in length.

9. The immunoassay of claim 5, wherein said peptide has a sequence that corresponds to SEQ ID NO:2.

10. The immunoassay of claim 5, wherein said peptide consists of SEQ ID NO:2
KVEAMEKFLYTAFAMQELGCNQNQFFCKIPLE.

11. A test kit for performing an immunoassay for detection of antibodies that specifically bind to feline immunodeficiency virus (FIV), in a biological sample from a felid mammal exposed to the virus, wherein said kit comprises:
  (i) a peptide according to claim 1, said peptide being unbound or bound, labeled or unlabeled, and
  (ii) means for detecting the formation of immune complex between said peptide and antibodies in said sample.

12. The test kit of claim 11, which is a hemagglutination assay kit; wherein said peptide is coupled to an antibody or antibody fragment which specifically binds to feline red blood cells.

13. The test kit of claim 12, wherein the coupling between said antibody or antibody fragment and said peptide is between a sulfhydryl group on the antibody or antibody fragment and a sulfhydryl group of at least one of the cysteine residues which are amino acids 699 and 706 of said sequence.

14. The test kit of claim 11, wherein said peptide is 36 amino acids in length.

15. The test kit of claim 11, wherein said peptide has a sequence that corresponds to SEQ ID NO:2.

16. The test kit of claim 11, wherein said peptide consists of SEQ ID NO:2
KVEAMEKFLYTAFAMQELGCNQNQFFCKIPLE.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
    ( A ) LENGTH: 32 amino acids
    ( B ) TYPE: amino acid
    ( D ) TOPOLOGY: linear ( x i ) SEQUENCE DESCRIPTION: SEQ ID NO:1:

```
Lys  Val  Glu  Ala  Met  Glu  Lys  Phe  Leu  Tyr  Thr  Ala  Phe  Ala  Met  Gln
1                  5                        10                           15

Glu  Leu  Gly  Cys  Asn  Gln  Asn  Gln  Phe  Phe  Cys  Glu  Ile  Pro  Lys  Glu
               20                       25                      30
```

( 2 ) INFORMATION FOR SEQ ID NO:2:

( i ) SEQUENCE CHARACTERISTICS:
    ( A ) LENGTH: 32 amino acids
    ( B ) TYPE: amino acid
    ( D ) TOPOLOGY: linear ( x i ) SEQUENCE DESCRIPTION: SEQ ID NO:2:

```
Lys  Val  Glu  Ala  Met  Glu  Lys  Phe  Leu  Tyr  Thr  Ala  Phe  Ala  Met  Gln
1                  5                        10                           15

Glu  Leu  Gly  Cys  Asn  Gln  Asn  Gln  Phe  Phe  Cys  Lys  Ile  Pro  Leu  Glu
               20                       25                      30
```

( 2 ) INFORMATION FOR SEQ ID NO:3:

( i ) SEQUENCE CHARACTERISTICS:
    ( A ) LENGTH: 32 amino acids
    ( B ) TYPE: amino acid
    ( D ) TOPOLOGY: linear ( x i ) SEQUENCE DESCRIPTION: SEQ ID NO:3:

```
Lys  Val  Glu  Ala  Ile  Glu  Lys  Phe  Leu  Tyr  Thr  Ala  Phe  Ala  Met  Gln
1                  5                        10                           15

Glu  Leu  Gly  Cys  Asn  Gln  Asn  Gln  Phe  Phe  Cys  Lys  Ile  Pro  Pro  Ser
               20                       25                      30
```

( 2 ) INFORMATION FOR SEQ ID NO:4:

( i ) SEQUENCE CHARACTERISTICS:
    ( A ) LENGTH: 32 amino acids
    ( B ) TYPE: amino acid
    ( D ) TOPOLOGY: linear (xi) SEQUENCE DESCRIPTION: SEQ ID NO:4:

Arg Val Glu Ala Ile Glu Lys Phe Leu Tyr Thr Ala Phe Ala Met Gln
1               5                       10                      15

Glu Leu Gly Cys Asn Gln Asn Gln Phe Phe Cys Lys Ile Pro Pro Ser
            20                  25                  30

(2) INFORMATION FOR SEQ ID NO:5:

(i) SEQUENCE CHARACTERISTICS:
    (A) LENGTH: 36 amino acids
    (B) TYPE: amino acid
    (D) TOPOLOGY: linear (xi) SEQUENCE DESCRIPTION: SEQ ID NO:5:

Arg Val Ser Tyr Leu Glu Tyr Val Glu Glu Ile Arg Gln Lys Gln Val
1               5                       10                      15

Phe Phe Gly Cys Lys Pro His Gly Arg Tyr Cys His Phe Asp Phe Gly
            20                  25                  30

Pro Glu Glu Val
            35